(12) United States Patent
Sheriff et al.

(10) Patent No.: US 8,158,127 B2
(45) Date of Patent: Apr. 17, 2012

(54) COMPOUNDS FOR NEUTRALIZING THE EFFECTS OF SECRETED PLA2 IIA

(75) Inventors: Ahmed Sheriff, Berlin (DE); Birgit Vogt, Berlin (DE)

(73) Assignee: Pentracor GmbH, Hennigsdorf (DE)

( * ) Notice: Subject to any disclaimer, the term of this patent is extended or adjusted under 35 U.S.C. 154(b) by 448 days.

(21) Appl. No.: 12/320,436

(22) Filed: Jan. 26, 2009

(65) Prior Publication Data

US 2009/0202535 A1     Aug. 13, 2009

Related U.S. Application Data

(62) Division of application No. 10/572,875, filed as application No. PCT/EP2004/010604 on Sep. 22, 2004, now abandoned.

(30) Foreign Application Priority Data

Sep. 22, 2003  (DE) .................................. 103 44 204

(51) Int. Cl.
    *A61K 39/395* (2006.01)
(52) U.S. Cl. ................. 424/145.1; 424/141.1; 424/130.1
(58) Field of Classification Search .................... None
    See application file for complete search history.

(56) References Cited

FOREIGN PATENT DOCUMENTS

| WO | WO 96/20959 | 7/1996 |
|---|---|---|
| WO | WO 9620959 | 7/1996 |
| WO | WO 98/53846 | 12/1998 |
| WO | WO 98/55504 | 12/1998 |
| WO | WO 02/08189 A | 1/2002 |
| WO | WO 02/08189 A1 | 1/2002 |

OTHER PUBLICATIONS

Green, Jonurnal of Immunological Methods 1999 231:11-23.
Owens et al. Journal of Immunological Methods 1994, 168:149-165.
Macchiarini et al. JEM 2005, 202:1307-1311.
Skolnick et al. Trends in Biotech. 18: 34-39, 2000.
Attwood Science 290: 471-473, 2000.
The Merck Manuals Online Medical Library, [online]. Whitehouse Station, NJ: Merck Research Laboratories, 2006-2007. [retrieved on Oct. 25, 2007]. Retrieved from the Internet: <URL: http://www.merck.com/mmpe/print/sec04/ch034/ch034b.html>. Rheumatoid Arthritis (RA), see pp. 1-9.
Touqui et al. Current Molecular Medicine 2001, 1:739-754.
P. N. Bernatchez et al., "VEGF stimulation of endothelial cell PAF synthesis is mediated by group V 14 kDa secretory phospholipase $A_2$," British Journal of Pharmacology (2001) 134, 197-205.
M. McCord et al., "Human Keratinocytes Possess an *sn*-2 Acylhydrolase that is Biochemically Similar to the U937-Derived 85-kDa Phospholipase $A_2$," The Journal of Investigative Dermatology, vol. 102, No. 6, Jun. 1994.
J. M. Stadel et al., "Recombinant Human Secretory Phospholipase $A_2$: Purification and Characterization of the Enzyme for Active Site Studies," Journal of Molecular Recognition, vol. 5, 145-153 (1992).
E. Abraham et al., "Efficacy and safety of LY315920Na/S-5920, a selective inhibitor of 14-kDa group IIA secretory phospholipase $A_2$, in patients with suspected sepsis and organ failure," Crit Care Med 2003 vol. 31, No. 3.
L. Touqui et al., "Mammalian Secreted Phospholipasei $A_2$ and Their Pathophysiological Significance in Inflammatory Diseases," Current Molecular Medicine 2001, 1;739-754.
Genbank accession No. NM_000300 *Homo sapiens* phospholipase A2, group IIA (platelets, synovial fluid) (PLA2G2A), mRNA, 2007.
Bidgood, J. M., "Type IIA Secretory Phospholipase $A_2$ Up-Regulates Cyclooxygenase-2 and Amplifies Cytokine-Mediated Prostaglandin Production in Human Rheumatoid Synoviocytes[1]," The Journal of Immunology, vol. 165, pp. 2790-2797, 2000.
Hundley, T.R. et al., "Characteristics of Arachidonic Acid Generation in Human Basophils: Relationship Between the Effects of Inhibitors of Secretory Phospholipase $A_2$ Activity and Leukotriene $C_4$ Release," The Journal of Pharmacology and Experimental Therapeutics, Mar 1998, vol. 284, No. 3, pp. 847-857.
Thwin, Muang-Muang et al., "Functional site of endogenous phospholipase $A_2$ inhibitor from python serum," European Journal of Biochemistry/Febs. Jan. 2002, vol. 269, 719-727.
Furue, Shingo, MS. et al., "Therapeutic time-window of a group IIA phospholipase $A_2$ inhibitor in rabbit acute lung injury: Correlation with lung surfactant protection," Critical Care Medicine, Apr. 2001, vol. 29, No. 4, pp. 719-727.
Niessen, Hans W.M. et al., "Type II secretory phospholipase A2 in cardiovascular disease: a mediator in atherosclerosis and ischemic damage to cardiomyocytes?" Cardiovascular Research, Oct. 15, 2003, vol. 60, No. 1, Sep. 4, 2003, pp. 68-77.
Graff, Jeremy R. et al., "Expression of Group IIa Secretory Phospholipase A2 Increases with Prostate Tumor Grade," Clinical Cancer Research: An Official Journal of the American Association for Cancer Research, Dec. 2001, vol. 7, No. 12, Dec. 2001, pp. 3857-3861.
Bidgood, Matthew J. et al., "Type IIA Secretory Phospholipase $A_2$ Up-Regulates Cyclooxygenase-2 and Amplifies Cytokine-Mediated Prostaglandin Production in Human Rheumatoid Synoviocytes[1]" Journal of Immunology, Sep. 1, 2000, vol. 165, No. 5, pp. 2790-2797.

(Continued)

*Primary Examiner* — Sharon Wen
(74) *Attorney, Agent, or Firm* — Jacobson Holman PLLC

(57) ABSTRACT

A compound comprising at least a structural entity which binds secretory phospholipase A2 IIA (sPLA2 IIA) or parts of it and more preferably human sPLA2 IIA and which
  a.) blocks at least one or more sPLA2 IIA function on cell surfaces or in a solution, preferably blood or other body fluids or from tissues, most preferably in vivo,
  b.) and/or depletes sPLA2 IIA from a solution, preferably blood or other body fluids or from tissues, most preferably in vivo.

8 Claims, No Drawings

OTHER PUBLICATIONS

Menschikowskl, M. et al. "Expression of Secretory Group IIA Phospholipase $A_2$ in Relation to the Presence of Microbial Agents, Macrophage Infiltrates, and Transcripts of Proinflammatory Cytokines in Human Aortic Tissues," Arterioscler Thromb Vasc. Biol, pp. 751.762 Jun. 16, 1999.

K. Hansford et al.: "D-tyrosine as a Chiral Precursor to Potent Inhibitors of Human Nonpancreatic Secretory Phospholipase $A_2$ (IIa) with Antiinflarnmatory Activity." Chembiochem, vol. 4, No. 2-3, Mar. 3, 2003, pp. 181-185.

M. Menschikowski et al.: "Expression of Secretory group IIa phospholipase $A_2$ in Relation to the Presence of Microbial Agents, Macrophage Infiltrates, and Transcripts of Proinflammatory Cytokines in Human Aortic Tissues.", Arteriosclerosis, Thrombosis, and Vascular Biology, 2000;20:751-762.

D. Fenard et al.: "Secreted phospholipase $A_2$, a new class HIV inhibitors that block virus entry into host cells." The Journal of Clinical Investigation, vol. 104, No. 5, Sep. 1999, pp. 611-618.

Reid, Robert C., "Inhibitors of Secretory Phospholipse $A_2$ Group IIA" Current Medicinal Chemistry, vol. 12, pp. 3011-3026, 2005.

COMPOUNDS FOR NEUTRALIZING THE EFFECTS OF SECRETED PLA2 IIA

This is a divisional of Ser. No. 10/572,875, filed, Jun. 21, 2006, which is a 371 of PCT/EP04/10604, filed Sep. 22, 2004.

The invention pertains with a compound neutralizing effects of sPLA2 IIA, a host cell producing the compound, a host cell producing the compound, a pharmaceutical composition for reducing the sPLA2 IIA concentration and uses of the compound.

The present invention deals with the disciplines of therapeutic proteins, cardiovascular physiology, and pharmacology. Specifically, the present invention is related to decreasing known risk factors of e.g. cardiovascular disease and other related diseases with endothelial participation associated with increased levels of secretory phospholipase A2 IIA (sPLA2 IIA) or parts of it and more preferably human sPLA2 IIA by administering molecules that bind sPLA2 IIA.

Cardiovascular disease is a major cause of death in the United States and a major source of morbidity, medical cost, and economic loss to millions of people. Two of the most common and destructive aspects of cardiovascular disease are the appearance of arteriosclerosis and thrombolitic events.

In recent years, a great deal of progress has been achieved in the treatment of cardiovascular disease. This progress has been possible not only because of the advancement of therapeutic intervention in the disease mechanisms, but also through the early identification of patients at risk of developing the disease. Indeed, patient risk identification and early treatment are important features of modern medical practice. Over the last twenty years, a variety of factors and clinical parameters have been identified which correlate with either the current state or the future probability of developing cardiovascular disease. Such risk factors may include measurable biochemical or physiological parameters, e.g., serum cholesterol, HDL, LDL, fibrinogen levels, etc., or behavioural of life-style patterns, such as obesity, smoking, etc. (For further information see: "Cardiovascular risk factors in the elderly', Kannel W., Coronary Artery Disease, 8:565-575, 1997 and references cited therein.) The risk factor most germane to the present invention is the level of sPLA2 IIA.

The intrinsic relationship between a measurable parameter or risk factor and the disease state is not always clear. In other words, it is not always clear whether the risk factor itself is causative or contributory to the disease or is instead an ancillary reflection that is indicative of the disease. Thus, a therapeutic modality, which effects a risk factor, may be directly modifying a pathological mechanism of the disease and its future course, or may be indirectly benefiting some contributory process related to the disease.

Additionally, many risk factors associated with cardiovascular disease are involved in other pathological states in either a causative or indicative role. Therefore, reduction or blockade of a particular risk factor in cardiovascular disease may have other beneficial effects in other diseases related to that risk factor.

Of particular interest to the methods of the present invention is the reduction of cardiovascular risk factors associated with abnormally high levels of sPLA2 IIA.

sPLA2 IIA is produced by the liver in response to cytokine production. Cytokines are produced as part of an inflammatory response in the body. Thus, sPLA2 IIA levels are a marker of systemic inflammatory activity. Chronic inflammation is thought to be one of the underlying and sustaining pathologies in cardiovascular disease.

At menopause, with the loss of estrogen, women's prevalence of cardiovascular disease increases. Also, the risk factors of cardiovascular disease increase, especially lipid (cholesterol and triglyceride), homocysteine, and C-reactive protein levels. Today, the most common method of preventing cardiovascular disease in post-menopausal women is Hormone Replacement Therapy (HRT). However, many women do not comply with this therapy because of the unpleasant side-effects, such as bloating, resumption of mensus, breast tenderness, fear of uterine and breast cancer, etc. Additionally, while HRT does lower cholesterol and homocysteine levels, HRT raises C-reactive protein levels.

One object of the invention is to provide a new therapeutic agent which lowers the risk factors mentioned above by neutralization of sPLA2 IIA.

Another object is to provide tools for decreasing levels of sPLA2 IIA in humans comprising administering to a human in need thereof an effective amount of a compound containing at least a molecule which binds sPLA2 IIA or a pharmaceutical salt or solvate thereof.

Still another object is to provide molecules and methods for decreasing levels of sPLA2 IIA in humans comprising administering to a human in need thereof an effective amount of a compound containing at least a molecule which binds sPLA2 IIA or a pharmaceutical salt or solvate thereof.

Further, the present invention relates to a method for inhibiting conditions or detrimental effects caused by an excess of sPLA2 IIA, or parts of it and more preferably human sPLA2 IIA, respectively comprising administering to a human in need thereof, an effective amount of a compound containing at least a molecule which binds sPLA2 IIA or a pharmaceutical salt or solvate thereof.

The present invention is based to the finding that molecules that bind sPLA2 IIA, i.e., antibodies, a recombinant antibody (as e.g. single chain antibody—scAb or scFv; bispecific antibody, diabody), monoclonal antibodies, are useful for lowering the levels of sPLA2 IIA and/or blocking and/or neutralizing sPLA2 IIA.

As used herein, the term "effective amount" means an amount of a compound of molecules which bind sPLA2 IIA which is capable of decreasing levels or blocking sPLA2 IIA and/or inhibiting conditions or detrimental effects caused by an excess of sPLA2 IIA.

The term "estrogen deficient" refers to a condition, either naturally occurring or clinically induced, where a woman can not produce sufficient estrogenic hormones to maintain estrogen dependent functions, e.g., menses, homeostasis of bone mass, neuronal function, cardiovascular condition, etc. Such estrogen deficient situations arise from, but are not limited to, menopause and surgical or chemical ovarectomy, including its functional equivalent, e.g., medication with GnRH agonists or antagonists, ICI 182780, and the like.

The term "inhibiting" in the context of inhibiting conditions or detrimental effects caused by an excess of sPLA2 IIA includes its generally accepted meaning, i.e., blocking, prohibiting, restraining, alleviating, ameliorating, slowing, stopping, or reversing the progression or severity of an increase of sPLA2 IIA and the pathological sequelae, i.e., symptoms, resulting from that event.

The term "pharmaceutical" when used herein as an adjective, means substantially non-toxic and substantially non-deleterious to the recipient.

By "pharmaceutical formulation" or "medicament" or "pharmaceutical composition" it is further meant that the carrier, solvent, excipients and salt must be compatible with the active ingredient of the formulation (a compound of at least a molecule, which binds sPLA2 IIA).

The term "solvate" represents an aggregate that comprises one or more molecules of the solute, with one or more molecules of a pharmaceutical solvent, such as water, buffer, physiological salt solution, and the like.

The present invention claims a compound comprising at least a structural entity which binds secretory phospholipase A2 IIA (sPLA2 IIA) or parts of it and more preferably human sPLA2 IIA and which a.) blocks at least one or more sPLA2 IIA and preferably human sPLA2 IIA functions on cell surfaces or in a solution, preferably blood or other body fluids or from tissues, most preferably in vivo, b.) and/or depletes sPLA2 IIA, preferably human sPLA2 IIA from a solution, preferably blood or other body fluids or from tissues, most preferably in vivo.

In one embodiment the compound of the invention is a polypeptide comprising a binding site to sPLA2 IIA, preferably an antibody containing an antigen-binding site to sPLA2 IIA. The compound of the invention is in particular a poly- or monoclonal antibody comprising an antigen-binding site to sPLA2 IIA. The monoclonal antibody comprises particularly an antigen-binding site to sPLA2 IIA and is obtainable after immunizing vertebrates, preferably mammals such as mice, rats, guinea pigs, hamsters, monkeys, pigs, goats, chicken, cows, horses and rabbits. The poly- or monoclonal antibody comprising an antigen-binding site to sPLA2 IIA is preferably humanized according to technologies well-known to the skilled person. The compound of the invention can also be prepared by immunizing humanized mice and/or immune defective mice (as e.g. SCID or nude mice) repopulated with vital immune cells (e.g. of human origin; as e.g. SCID-hu mice).

In a further embodiment the antibody of the invention is a recombinant antibody (as e.g. single chain antibody—scAb or scFv; bispecific antibody, diabody etc.) capable of binding to sPLA2 IIA, in particular by containing the antigen-binding site of an antibody which is cross-reactive with sPLA2 IIA. The antibody molecule of the invention is a humanized or human antibody. Subject matter of the invention is also a host cell, preferably a stable host cell, producing the compound of the invention.

Furthermore, subject matter of the invention is at least one recombinant vector comprising the nucleotide sequences encoding the binding molecule fragments according to the invention, operably linked to regulating sequences capable of expressing the antibody molecule in a host cell, preferably as a secretory protein.

Subject matter of the present invention is also a host comprising, preferably stably transgenic, the vector according to the invention, a prokaryotic or eukaryotic cell line producing a recombinant antibody of the invention as well as a eukaryotic organism, most preferably an animal, a plant or a fungus, producing a recombinant antibody according to the invention.

Subject matter of the invention is also a method of producing a recombinant molecule of the invention capable of binding to the sPLA2 IIA antigen, comprising culturing a host cell and isolating the binding molecule from the culture medium and/or the producing cell.

In another embodiment, the present invention is related with a method for inhibiting immunologic, inflammatory and/or pathophysiological responses by treating patients with increased sPLA2 IIA levels with the sPLA2 IIA-binding molecules according to the invention.

Another subject of the present invention is a pharmaceutical composition for reducing the sPLA2 IIA concentration, containing a therapeutically effective amount of the binding molecule according to the invention and a pharmaceutically acceptable carrier.

Still another embodiment of the invention is a method for reducing inflammatory immune and/or pathophysiological responses by reducing the sPLA2 IIA concentration, a method for reducing endothel injury and/or destruction by reducing the sPLA2 IIA concentration, a method for acute treatments in case of acute endothelial injury and/or destruction, preferably for stroke, cardiac infarction, avoidance of sudden cardiac death, for burnt offering, for severe surgery or other injuries with severe wound areas, for diabetic shock, for acute liver failure, for pancreatitis, neurodegenerative diseases, for leukemic persons after irradiation, a method for continuous treatments in case of long term endothelial injury and/or destruction, preferably for patients with medium CRP-amounts, with atherosclerosis, with unstable angina, with diabetes type I or type II, with overweight and/or obesity, for alcoholics, under Hormone Replacement Therapy (HRT), for old persons, for smokers, a method for preventing allograft transplant rejection or xeno-transplant rejection, a method for the induction of allo-transplant or xeno-transplant tolerance or inhibition of T cell activation, and a method for preventing or treatment of autoimmune diseases, the methods comprising administering to a patient in need of such treatment a therapeutically effective amount of a pharmaceutical composition of the invention.

The compound of the invention can be combined with other molecules, preferably therapeutics for the respective disease or other anti-inflammatory molecules like e.g. anti-IL-6-molecules, anti-IL-1β-molecules, anti-CRP-molecules, blocking molecules for IL-6, CRP, IL-1β and/or complement blockers.

The methods provided by the current invention are useful in both the treatment and prevention of harmful sequelae associated with elevated levels of sPLA2 IIA. Since sPLA2 IIA serum concentration is related to levels and production of cytokines, which are especially produced in inflammatory processes, the methods of the current invention are useful in treating or preventing inflammatory events and sequelae, thereof. Such inflammatory events include, but are not limited to: arterial and venous chronic inflammation, autoimmune diseases, e.g., arthritis (osteo and rheumatoid), SLE, multiple sclerosis, myasthenia gravis, Graves' disease, psoriasis vulgaris, dilated cardiomyopathy, diabetes mellitus, Morbus Bechterew, inflammatory bile disease, ulcerative colitis, Crohn's disease, idiopathic thrombocytopenia purpura (ITP), aplastic anemia, idiopathic dilated cardiomyopathy (IDM), autoimmune thyroiditis, Goodpastures' disease, and the like.

Methods of the current invention are useful for treating or preventing pathologic sequelae of atherosclerotic or thrombotic disease. Such pathologies include, but are not limited to stroke, circulatory insufficiency, ischemic events, myocardial infarction, pulmonary thromboembolism, stable and unstable angina, coronary artery disease, sudden death syndrome, and the like.

The present invention further contemplates the use of other currently known clinically relevant agents administered to treat the pathological conditions embodied in the present invention in combination with a compound of at least a molecule which binds sPLA2 IIA.

Moreover, the present invention contemplates that the compounds of at least a molecule which binds sPLA2 IIA are employed in either a treatment or prophylactic modality.

A preferred embodiment of the present invention is where the human to be administered a compound of the invention is female, and more preferred is when that human female is estrogen deficient.

Another preferred embodiment of the present invention is where the condition caused by an abnormally high level of sPLA2 IIA is cardiovascular disease, especially arteriosclerosis and thrombosis or other acute treatments in case of acute endothelial injury and/or destruction, like stroke, cardiac infarction, sudden cardiac death, burnt offering, severe surgery or other injuries with severe wound areas, diabetic shock, acute liver failure, pancreatitis, leukemic persons after irradiation or long term endothelial injury and/or destruction, like arteriosclerosis, diabetes type I or type II, overweight and/or obesity, alcoholism, Hormone Replacement Therapy (HRT), old persons, smokers.

A particularly preferred embodiment of the present invention is the use of a compound of at least a molecule which binds sPLA2 IIA in an estrogen deficient women, who is receiving estrogen or HRT, for the reduction of systemic or local inflammation.

Lymph Node Fibrosis Impedes Peripheral CD4+ T-Cell Count

Fibrosis could be Better Predictor of Ability to Recover after HAART

Because HIV preferentially targets CD4+ T cells, their numbers, along with other metrics like HIV RNA levels, traditionally are used to indicate the infection's severity. Moreover, clinicians use these numbers to predict the efficacy of future immunological reconstitution treatment in first-time patients undergoing antiretroviral therapy.

But a recent finding shows that highly active antiretroviral therapy (HAART) failed to markedly increase the peripheral CD4+ count in 25% of patients, despite sometimes being able to reduce HIV RNA in the blood to undetectable levels. This finding has brought into question the utility of these factors as recovery predictors. There are factors beyond suppression of viral replication.

The amount of lymph node fibrosis prior to HAART initiation is perhaps a better indicator of a patient's ability to recover peripheral CD4+ T cells following HAART. The damage to the lymph nodes, where nearly all HIV replication takes place in the activated CD4+ cells that reside there, has already occurred before therapy has even started.

An ever-expanding body of work is showing the importance of lymph node architecture in providing a suitable microenvironment for the immune processes. Here, T cells interact with B cells, antigen-presenting cells, stroma, and each other, as well as receive soluble messages through cytokines and other growth factors. So, if the structure is compromised, the lymph nodes' ability to support a viable immune system may be severely compromised as well.

Perpetual Inflammation

Examination of the T-cell zones of lymph nodes from treatment-naive patients at various stages of HIV infection, from presymptomatic to full-blown AIDS was done. The number of CD4+ T cells found there did not correlate with either peripheral CD4+ cells or with detectable amounts of viral RNA in the plasma. But the nodes had considerably more collagen deposition than HIV-negative controls. The collagen showed an inverse relationship to the nodal CD4+ T-cell population; the number of CD4+ cells decreased as the amount of fibrosis increased. Similarly, the potential for immunological reconstitution as measured by the peripheral CD4+ T-cell count after therapy showed an inverse relationship with the amount of nodal collagen deposition.

It is speculated that lymph nodes are likely damaged because of perpetual inflammation. In the long struggle between immune defenses and HIV-1 that partially controls replication, the immune system is maintained in a state of chronic activation.

The model is not unprecedented. The situation is analogous to what happens to the liver in a chronic hepatitis infection. In such cases, ongoing viral replication leads to chronic inflammation and fibrosis, eventually replacing functional hepatic tissue with collagen; the end result is cirrhosis.

While it is unclear exactly what mechanism is operating here damage to lymph node structure could have several consequences for the immune response, including the inability of the lymph nodes with large amounts of collagen to physically house T cells, or to alter positioning of T cells such that proper activation, growth or chemotactic signals are not received. Excessive deposition of collagen and other extracellular matrix components within the T zone might be expected to disrupt T-cell interactions with dendritic cells or local production of IL-7 [the T-cell survival factor interleukin 7].

Damage and disruption to the lymphatic tissue microenvironment results in the impaired recruitment, retention, and proliferation of CD4+ cells. The most significant impact would be on naive CD4+ T cells, which are known to require greater external signaling to proliferate and remain viable than do activated or memory cells.

Presuming that chronic inflammation is responsible for damaging the lymph node architecture, anti-inflammatory therapy as e.g. reduction of sPLA2 IIA would lessen, prevent, or even reverse some of the fibrosis, perhaps leading to an improved immunological recovery.

Pharmaceutical formulations can be prepared by procedures known in the art, such as, for example, a compound of at least a molecule which binds sPLA2 IIA can be formulated with common excipients, diluents, or carriers, and formed into tablets, capsules, and the like.

Examples of excipients, diluents, and carriers that are suitable for formulation include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of at least a molecule which binds sPLA2 IIA are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices, which may be made from polymeric substances or waxes.

The particular dosage of a compound containing molecules which bind sPLA2 IIA required to decrease levels of homocysteine and/or sPLA2 IIA according to this invention will depend upon the particular circumstances of the conditions to be treated. Considerations such as dosage, route of administration, and frequency of dosing are best decided by the attending physician. Generally, an effective minimum dose for oral or parenteral administration of a compound of molecules which bind sPLA2 IIA is about 1 to 20,000 mg. Typically, an effective maximum dose is about 20,000, 6,000, or 3,000 mg. Such dosages will be administered to a patient in need of treatment as often as needed to effectively decrease levels of sPLA2 IIA and/or inhibit conditions or detrimental effects caused by an excess of sPLA2 IIA.

The invention claimed is:

1. A method of treatment for reducing acute endothelial injury and/or destruction associated with cardiac infarction, the method comprising reducing secretory phospholipase A2 II A (sPLA2 IIA) concentration and/or neutralizing sPLA2 IIA by administering to a patient in need thereof a therapeutically effective amount of an anti-sPLA2 IIA antibody.

2. The method according to claim 1, wherein the sPLA2 IIA is human sPLA IIA and the antibody blocks and/or neutralizes at least one function of sPLA2 IIA in a body fluid or tissue.

3. The method according to claim 1, wherein the antibody is a monoclonal antibody.

4. The method according to claim 3, wherein the monoclonal antibody is obtainable by immunizing a vertebrate.

5. The method according to claim 3, wherein the monoclonal antibody is obtainable by immunizing a transgenic vertebrate.

6. The method according to claim 3, wherein the monoclonal antibody is obtainable by immunizing an immune defective mouse repopulated with vital immune cells.

7. The method according to claim 1, wherein the antibody is a recombinant antibody.

8. The method according to claim 7, wherein the antibody is a humanized or human antibody.

* * * * *